United States Patent
Irie et al.

(10) Patent No.: US 8,987,507 B2
(45) Date of Patent: Mar. 24, 2015

(54) FLUOROALKANESULFONIC ACID PRODUCTION METHOD

(75) Inventors: Tatsuya Irie, Ube (JP); Kenji Isoyama, Ube (JP); Tatsuo Miyazaki, Ube (JP); Takashi Kashiwaba, Ube (JP); Tsutomu Nanmyo, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/232,450

(22) PCT Filed: Aug. 2, 2012

(86) PCT No.: PCT/JP2012/069642
§ 371 (c)(1),
(2), (4) Date: Jan. 13, 2014

(87) PCT Pub. No.: WO2013/018848
PCT Pub. Date: Feb. 7, 2013

(65) Prior Publication Data
US 2014/0171678 A1    Jun. 19, 2014

(30) Foreign Application Priority Data

Aug. 4, 2011    (JP) ................................ 2011-170642

(51) Int. Cl.
| | | |
|---|---|---|
| C07C 309/00 | (2006.01) | |
| C07C 303/02 | (2006.01) | |
| C07C 303/22 | (2006.01) | |
| C07C 303/44 | (2006.01) | |

(52) U.S. Cl.
CPC ............. *C07C 303/02* (2013.01); *C07C 303/22* (2013.01); *C07C 303/44* (2013.01)
USPC .......................................... 562/113; 562/118

(58) Field of Classification Search
None
See application file for complete search history.

(56) References Cited

U.S. PATENT DOCUMENTS 4,927,962 A * 5/1990 Aramaki et al. .............. 562/113
5,498,754 A    3/1996 Nakamura et al.

FOREIGN PATENT DOCUMENTS

| JP | 30-4218 | 1/1953 |
|---|---|---|
| JP | 64-61452 A | 3/1989 |
| JP | 64-85946 A | 3/1989 |
| JP | 6-298720 A | 10/1994 |
| JP | 2002-88051 A | 3/2002 |

OTHER PUBLICATIONS

Database Caplus Chemical Abstracts Service, Columbus, Ohio, US; Database Accession No. 2003:502245 Abstract of RU 2203271 Varfolomeev ewt al., FGUP "Angarskii Elektroliznyi Khimicheskii Kombinat", Russia, Apr. 27, 2003.*
International Search Report (PCT/ISA/210) with English translation dated Nov. 13, 2012 (Five (5) pages).
Japanese language Written Opinion (PCT/ISA/237) dated Nov. 13, 2012 (Five (5) pages).

* cited by examiner

*Primary Examiner* — Karl J Puttlitz
(74) *Attorney, Agent, or Firm* — Crowell & Moring LLP

(57) ABSTRACT

Disclosed is a method for producing a fluoroalkanesulfonic acid including (1) the step of reacting concentrated sulfuric acid and/or fuming sulfuric acid with a fluoroalkanesulfonate to cause an acid decomposition, thereby obtaining a reaction mixture containing the fluoroalkanesulfonic acid and a sulfur component; and (2) the step of adding an oxidizing agent to the reaction mixture obtained by the above step and then conducting a distillation, thereby obtaining the fluoroalkanesulfonic acid from the reaction mixture. It is possible by this method to efficiently reduce the sulfur component, thereby industrially advantageously obtaining fluoroalkanesulfonic acid of high purity.

9 Claims, No Drawings

FLUOROALKANESULFONIC ACID PRODUCTION METHOD

TECHNICAL FIELD

The present invention relates to a method for producing fluoroalkanesulfonic acids, which are useful materials as catalysts of organic synthesis reactions, etc. or as raw materials for producing high-purity fluoroalkanesulfonates.

BACKGROUND OF THE INVENTION

Of fluoroalkanesulfonic acids, for example, trifluoromethanesulfonic acid is a useful material as a raw material for producing lithium trifluoromethanesulfonate, which is used as a lithium cell electrolyte. As the method for producing lithium trifluoromethanesulfonate suitable for cells is shown by the reaction formula (1), $$2CF_3SO_3H + Li_2CO_3 \rightarrow 2CF_3SO_3Li + CO_2 + H_2O \quad (1)$$

it is obtained by subjecting a high-purity trifluoromethanesulfonic acid to a neutralization reaction by a high-purity lithium carbonate.

In this case, the raw material acid is required to contain impurities, such as sulfuric acid, free fluorine, etc., as little as possible. Thus, it is necessary to reduce these impurities until less than ten ppm. For example, the method of Patent Publication 1 is known as one that is industrially widely conducted as a method for producing fluoroalkanesulfonic acid. As shown in the following scheme, trifluoromethanesulfonyl fluoride is produced by an electrolytic fluorination method, followed by conducting a hydrolysis reaction by heating with a potassium hydroxide aqueous solution to obtain potassium trifluoromethanesulfonate, and then the potassium salt is reacted with excessive 100% sulfuric acid, followed by conducting a distillation to obtain a crude product of trifluoromethanesulfonic acid. Furthermore, the crude product is subjected to a rectification to obtain trifluoromethanesulfonic acid of high purity.

<Patent Publication 1>

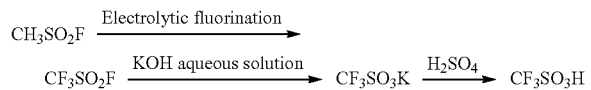

There is, however, a problem that the production cost increases since the step for obtaining trifluoromethanesulfonic acid of high purity is long in this method, and since the environmental load is heavy due to the use of organic solvent, etc., too. Furthermore, in the acid decomposition reaction, since the distillation under heating and reduced pressure is conducted after excessively adding concentrated sulfuric acid and fuming sulfuric acid, a pyrolysis reaction of the target product and/or side reactions proceed. This causes a large amount of free fluorine derived from hydrogen fluoride, and its mixing into the fluoroalkanesulfonic acid cannot be prevented. Therefore, it has been impossible to prevent the quality from lowering strikingly and that from having a large amount of free fluorine, etc. Furthermore, there has also been a problem of containing a large amount of sulfuric acid in the fluoroalkanesulfonic acid after the distillation under heating and reduced pressure.

The present applicant has proposed a method with an incorporated recycling step, in which, similar to Patent Publication 1, a mixed aqueous solution of potassium trifluoromethanesulfonate and potassium fluoride is obtained, followed by crystallizing potassium trifluoromethanesulfonate by concentration or adding an alkali, then separating the crystals by filtration, and circulating the filtrate to the gas absorption step, as a method for industrially advantageously producing a fluoroalkanesulfonic acid by simpler apparatus and operation than those in the past (Patent Publication 2).

Furthermore, the present applicant has found a method for producing a fluoroalkanesulfonic acid with a small amount of free fluorine by adding sulfuric acid and silica or a silica compound to a fluorocarbon compound, as a method for obtaining a fluoroalkanesulfonic acid of high purity by removing free fluorine, and has made an application therefor (Patent Publication 3).

Similarly, the present applicant has found a method of adding water during the purification under heating (in the following, it is mentioned as "water addition distillation", too) in order to solve the mixing of sulfuric acid into the fluoroalkanesulfonic acid after the distillation under heating and reduced pressure and has made an application therefor (Patent Publication 4).

PRIOR ART PUBLICATIONS

Patent Publications

Patent Publication 1: Japanese Patent Application Post-examination Publication Showa 30-4218
Patent Publication 2: Japanese Patent Application Publication Heisei 1-61452
Patent Publication 3: Japanese Patent Application Publication Heisei 1-85946
Patent Publication 4: Japanese Patent Application Publication Heisei 6-298720

SUMMARY OF THE INVENTION

The method of Patent Publication 4 is effective not only for removing sulfuric acid to the fluoroalkanesulfonic acid, but also for trace impurity components of a crude product obtained by sulfuric acid decomposition and distillation of a fluoroalkanesulfonate. Thus, it is an effective method for producing fluoroalkanesulfonic acid of high purity, together with the method of Patent Publication 3 (see the following reaction formulas (2) to (6)).

As a result of conducting a further study by the present inventors, however, there was found a problem that a yellow-color solid was precipitated in the column or line of the distillation apparatus to cause clogging of the line, etc. It was considered that this was caused by a sulfur component generated by the reaction of the reaction formula (3). Furthermore, in some cases, sulfur was contained in the purified product after the water addition distillation, too (see Comparative Example 1).

Thus, it is a task of the present invention to provide a method for producing fluoroalkanesulfonic acid of high purity, which is industrially advantageous, by reducing precipitation and mixing of a sulfur component.

As a result of an eager study by the present inventors to solve the above-mentioned task, we have found that it is possible to reduce precipitation and mixing of sulfur component by adding an oxidizing agent to a reaction mixture containing a fluoroalkanesulfonic acid and sulfur component, which has been obtained by an acid decomposition reaction of a fluoroalkanesulfonate, and then conducting a distillation. Herein, the reduction means that the content of disulfur trioxide as sulfur component is 1 ppm or less and it does not show a color reaction generated by a reaction with fuming sulfuric acid (see Examples).

The present invention includes Invention 1 to Invention 7 shown in the following.

[Invention 1]

A method for producing a fluoroalkanesulfonic acid represented by the general formula [1], $$R^fSO_3H \quad [1]$$

(In the formula, $R^f$ represents a $C_{1-4}$ straight chain or $C_{3-4}$ branched chain fluoroalkyl group.)
the method being characterized by comprising the following steps of:

(1) the step of reacting concentrated sulfuric acid and/or fuming sulfuric acid with a fluoroalkanesulfonate represented by the general formula [2], $$(R^fSO_3)_nM \quad [2]$$

($R^f$ is identical with that of the general formula [1], M represents an alkali metal or an alkali earth metal, and n is an integer of 1 or 2.)
to cause an acid decomposition, thereby obtaining a reaction mixture containing the fluoroalkanesulfonic acid and a sulfur component; and (2) the step of adding an oxidizing agent to the reaction mixture obtained by the above step and then conducting a distillation, thereby obtaining the fluoroalkanesulfonic acid from the reaction mixture.

[Invention 2]

A method for producing a fluoroalkanesulfonic acid represented by the formula [3], $$CF_3SO_3H \quad [3]$$

the method being characterized by comprising the following steps of:

(1) the step of reacting concentrated sulfuric acid and/or fuming sulfuric acid with a fluoroalkanesulfonate represented by the general formula [4], $$(CF_3SO_3)_nM \quad [4]$$

(M and n are identical with those of the general formula [2])
to cause an acid decomposition, thereby obtaining a reaction mixture containing the fluoroalkanesulfonic acid and a sulfur component; and (2) the step of adding an oxidizing agent to the reaction mixture obtained by the above step and conducting a distillation, thereby obtaining the fluoroalkanesulfonic acid from the reaction mixture.

[Invention 3]

The method of Invention 1 or Invention 2, wherein, in the second step, the oxidizing agent used is hydrogen peroxide, ozone, or oxygen.

[Invention 4]

The method of Invention 1 or Invention 2, wherein, in the second step, the oxidizing agent used is hydrogen peroxide.

[Invention 5]

The method of any one of Inventions 1 to 4, which is characterized by that, in the step (1), when concentrated sulfuric acid and/or fuming sulfuric acid is reacted the fluoroalkanesulfonate represented by the general formula [2], moreover a silica compound is added.

[Invention 6]

The method of any one of Inventions 1 to 5, which is characterized by that, in the step (2), together with the oxidizing agent, water is added to conduct the distillation.

[Invention 7]

The method of any one of Inventions 1 to 6, wherein, in producing the fluoroalkanesulfonic acid, the fluoroalkanesulfonate represented by the general formula [2] is one obtained by reacting at least one selected from the group consisting of alkali metal hydroxides, alkali metal carbonates, alkali metal hydrogencarbonates, alkali earth metal hydroxides, alkali earth metal carbonates, and alkali earth metal hydrogencarbonates, with a fluoroalkanesulfonyl halide represented by the general formula [5], $$R^fSO_3X \quad [5]$$

(In the formula, Rf is identical with that of the general formula [1], and X represents fluorine, chlorine, bromine, or iodine.).

Sulfur as one of the tasks of the present invention is generated by the reaction of the above-mentioned reaction formula (3). Disulfur trioxide ($S_2O_3$) as the reactant in the reaction is a substance of a blue-green color. This substance is an unfavorable substance, since the existence of this substance even by less than 10 ppm cause a solution containing a fluoroalkanesulfonic acid to have a blue-green color. As a result of an eager study, the present inventors have found that this substance has a high frequency of generation in the case of conducting the acid decomposition reaction in a stainless steel reactor. From this, it is assumed that disulfur trioxide is generated by a reaction shown in the following scheme.

$$5H_2SO_4+2H^++6e^- \rightarrow 4HSO_4^-+4H_2O+S \text{ (precipitation)}$$

$$S+SO_3 \rightarrow S_2O_3 \text{ (coloring with a blue color)}$$

In the case of a stainless steel reactor, it is considered that a corrosive reduction reaction of the above scheme proceeds to generate sulfur. As sulfur trioxide in fuming sulfuric acid reacts therewith, disulfur trioxide as a coloring component is generated. From this, it is assumed that the generation of these sulfur components can be suppressed by changing the material of the reactor to a special material not belonging to non-stainless steels.

The material of many reactors normally used when conducting the production at an industrial level is, however, stainless steel. In the case of not having a reactor that can be fitted to conventional facilities and other cases, it is not preferable from the viewpoint of the construction cost. Therefore, versatility has been low by only changing the material of the reactor.

On that point, it is possible in the present invention to effectively reduce the generated sulfur component, such as sulfur trioxide and sulfur, by a distillation with the addition of an oxidizing agent. Therefore, purity of the target product is not affected even by conducting the reaction using the material of stainless steel.

Advantageous Effect of the Invention

The present invention proposes a method of effectively reducing sulfur component generated in the reaction mixture after the acid decomposition reaction. With this, it is possible to industrially advantageously produce a fluoroalkanesulfonic acid of high purity without causing clogging in the distillation line, etc. Furthermore, it is possible to use a general stainless steel reactor, which is industrially low in price, for the reaction. Therefore, it is possible to produce a fluoroalkanesulfonic acid advantageously in terms of the construction cost.

DETAILED DESCRIPTION

The present invention is explained in detail.
In the present invention, the production of a fluoroalkanesulfonic acid is conducted by the following two steps.
(1) the step of reacting concentrated sulfuric acid and/or fuming sulfuric acid with a fluoroalkanesulfonate represented by the general formula [2],

$(R^fSO_3)_nM$     [2]

($R^f$ represents a $C_{1-4}$ straight chain or $C_{3-4}$ branched chain fluoroalkyl group, M represents an alkali metal or an alkali earth metal, and n is an integer of 1 or 2.)
to cause an acid decomposition, thereby obtaining a reaction mixture containing the fluoroalkanesulfonic acid and a sulfur component (in the following, mentioned as "acid decomposition step"); and
(2) the step of adding an oxidizing agent to the reaction mixture obtained by the above step and then conducting a distillation, thereby obtaining the decolorized fluoroalkanesulfonic acid (in the following, mentioned as "addition distillation step").

Firstly, the acid decomposition step is explained in detail.
The fluoroalkanesulfonate used in the present step is one represented by the general formula [2]. $R^f$ in the formula represents a $C_{1-4}$ fluoroalkyl group. This fluoroalkyl group is one in which at least one fluorine has been substituted therefor. In particular, a perfluoroalkyl group, such as trifluoromethyl group, is preferable. M in the formula represents an alkali metal, such as lithium, sodium, calcium or potassium, or an alkali earth metal, such as magnesium or calcium. Preferably, it is sodium or potassium in alkali metals, and magnesium in alkali earth metals. Particularly preferably, it is potassium. In case that M is an alkali metal, n is an integer of 1. In case that M is an alkali earth metal, n is an integer of 2.

As preferable ones of the fluoroalkanesulfonate, specifically, it is possible to mention sodium trifluoromethanesulfonate, potassium trifluoromethanesulfonate, magnesium trifluoromethanesulfonate, sodium pentafluoroethanesulfonate, potassium pentafluoroethanesulfonate, magnesium pentafluoroethanesulfonate, sodium heptafluoropropanesulfonate, potassium heptafluoropropanesulfonate, magnesium heptafluoropropanesulfonate, sodium nonafluorobutanesulfonate, potassium nonafluorobutanesulfonate, and magnesium nonafluorobutanesulfonate. In particular, more preferably, they are potassium trifluoromethanesulfonate and potassium pentafluoroethanesulfonate.

The fluoroalkanesulfonate used in the acid decomposition step is not particularly limited. For example, as in the method of Patent Publication 1, it suffices to use one obtained by a publicly known production method. In terms of continuous production being possible, it is preferable to obtain a fluoroalkanesulfonate by reacting an alkali metal hydroxide, an alkali metal carbonate, an alkali metal hydrogencarbonate, an alkali earth metal hydroxide, an alkali earth metal carbonate, an alkali earth metal hydrogencarbonate or the like, with a fluoroalkanesulfonyl halide represented by the general formula [5]. In the case of being derived from a fluoroalkanesulfonyl halide, furthermore, it is industrially preferable to use a fluoroalkanesulfonate obtained by a production method containing a recycling step, as disclosed in Patent Publication 2. In the case of the latter method, the fluoroalkanesulfonate obtained may contain the corresponding metal's hydroxide and halide and water. It can be used, as it is, for the acid decomposition step of the present invention.

In the acid decomposition step, concentrated sulfuric acid and/or fuming sulfuric acid is used as the sulfuric acid. It is optional to use only one of concentrated sulfuric acid and fuming sulfuric acid, but it is a preferable mode to use both of them. Normally, as the concentrated sulfuric acid, it suffices to use one having a concentration of about 98%, which is easily available, and it suffices that the fuming sulfuric acid has a concentration of about 20-25%. It is, however, not limited to this. It is preferable that usage of the concentrated sulfuric acid is about 50-500 mass %, in case that the fluoroalkanesulfonate is 100. The fuming sulfuric acid is capable of effectively reducing water in the concentrated sulfuric acid and the fluoroalkanesulfonate, which are used. The amount to be used may be about 50-200 mass %, in case that the amount of water contained in the fluoroalkanesulfonate is 100 mass %.

Furthermore, in case that the fluoroalkanesulfonate to be used in the step has been contaminated with free fluorine, it is also one of preferable modes to add a silica compound when conducting the reaction. The silica compound is not particularly limited, as long as it easily reacts with fluorine. It is possible to mention sodium silicate, silica obtained from silicofluoride, glass, etc., as well as naturally existing ones, such as diatomaceous earth. The addition can suitably be used depending on the amount of free fluorine mixed in the fluoroalkanesulfonate. Normally, it suffices to use about 0.2-2.0 mols in case that free fluorine is 1 mol.

It suffices in the acid decomposition step to at least add concentrated sulfuric acid and/or fuming sulfuric acid to the fluoroalkanesulfonate and then conducting a heating stirring. As the reaction temperature, normally, about 50-100° C. is acceptable. The reaction time may suitably be examined depending on the reaction temperature and reagents used. Normally, the reaction sufficiently progresses with about 1-3 hours. With this, it is possible to obtain a reaction mixture containing the fluoroalkanesulfonic acid and sulfur component. The obtained reaction mixture itself may be used for the next addition distillation step. Alternatively, it is optional to once conduct a simple distillation or the like to obtain a crude product containing the fluoroalkanesulfonic acid and sulfur component, from which a component such as sulfuric acid has been removed to a certain extent, and then using the crude product in the next addition distillation step.

In the acid decomposition step, in the case of adding a silica compound for removing free fluorine, it is preferable to remove silicon tetrafluoride ($SiF_4$) to be generated, from the system. Normally, when the reaction temperature is in a range of 10-160° C., it suffices to remove silicon tetrafluoride under ordinary pressure or reduced pressure with stirring. In the case of conducting the reaction under reduced pressure, it is possible by conducting a distillation operation as it is to obtain a crude product which contains the fluoroalkanesulfonic acid and sulfur component and from which free fluorine has been removed. It suffices to use this in the next addition distillation step.

Then, the addition distillation step is explained. In the present invention, when conducting a heating distillation of a mixture (this refers to both of the reaction mixture and the crude product, and in the following simply mentioned as "the reaction mixture") which has been obtained by the acid decomposition step and which contains the fluoroalkanesulfonic acid and sulfur component, an oxidizing agent is added. With this, it is possible to reduce disulfur trioxide in the reaction mixture to remove a color caused by the sulfur component and effectively reduce precipitation and mixing of sulfur.

As the oxidizing agent to be added, it is possible to use hydrogen peroxide, ozone, air, oxygen, etc. Preferably, it is ozone, hydrogen peroxide or oxygen. More preferably, it is hydrogen peroxide. In case that the oxidizing agent is solid or liquid, it may be added to the reactor in advance or after feeding the reaction mixture liquid. In case that the oxidizing agent is gas, it suffices to introduce the gas by bubbling into the reactor charged with the reaction mixture.

As to the amount of the oxidizing agent to be added, it may suitably be used depending on the amount of disulfur trioxide existing in the reaction mixture. It is possible to estimate the amount of disulfur trioxide in the reaction mixture by the degree of the coloration of the blue-green color. For example, in UV measurement, disulfur trioxide shows absorption at 585 nm. Therefore, it is possible to calculate the concentration of disulfur trioxide from absorbance of the reaction mixture to be used in the addition distillation by making a calibration curve between the concentration of disulfur trioxide and the absorbance at 585 nm. The oxidizing agent to be used relative to 1 mol of disulfur trioxide may be 1-100 equivalents, preferably 1-5 equivalents.

In the addition distillation step, it is optional to add water together with the oxidizing agent. The addition of water can prevent contamination of the distillate with sulfuric acid. Therefore, it is one of preferable modes. It suffices that the amount of water to be added is in a range of 0.1-30 mass % in case that the total amount of the reaction mixture liquid is 100 mass %.

The temperature and the degree of decompression of the addition distillation depend on the boiling point of the target fluoroalkanesulfonic acid. Therefore, they may be adjusted each time. For example, in the case of trifluoromethanesulfonic acid, it is possible to obtain the target fluoroalkanesulfonic acid by setting the degree of decompression at about 1.2-6.7 kPa and the temperature of the inside of the reactor at 80-100° C.

By conducting the above-mentioned addition distillation, it is possible to obtain a fluoroalkanesulfonic acid of high purity that sulfur component is not precipitated in the distillation apparatus and that sulfur component is not mixed in the distillate, either.

EXAMPLES

In the following, one mode of the present invention is explained in detail by examples, but the present invention is not limited to such examples.

The calculation and the detection of sulfur component were conducted by the following operations.

[Calculation of the Content of Disulfur Trioxide]

Using a UV measurement apparatus (made by Shimadzu Corporation, model number: UV-2550), there was measured absorbance of the sample at 585 nm. Using a calibration curve between absorbance at 585 nm and the concentration of disulfur trioxide, the content of disulfur trioxide in the sample was calculated.

[Detection of Sulfur Component]

Fuming sulfuric acid was added to the sample to check coloration of a blue-green color. In case that sulfur exists, the sample shows a blue-green color.

Example 1

[Step 1] Acid Decomposition

A 1000 ml reaction container made of SUS304 and equipped with a condenser and a flask for drawing out was charged with 320 g of sulfuric acid, 650 g of fuming sulfuric acid, and 8.8 g of $SiO_2$ powder. There 482 g of potassium trifluoromethanesulfonate (composition: a product containing 4.0% of water, 2.0% of KOH, and 1.7% of KF) was added. Simultaneously with the reaction, a distillation was started. At a temperature of the inside of the reactor of 130° C., a degree of decompression of 2.7 kPa and a column top temperature of 72° C., the initial distillate was taken out by 60 g. After that, it was started to take the main distillate. At a temperature of the inside of the reactor of 140-152° C., a degree of decompression of 2.5-2.7 kPa and a column top temperature of 68-70° C., 189 g of the main distillate colored with a blue color was obtained. This main distillate contained 97.1% of trifluoromethanesulfonic acid, and furthermore the $S_2O_3$ concentration of the main distillate was 735 ppm. After the distillation, [Step 2] was conducted by using the obtained main distillate.

[Step 2] Addition Distillation: Addition of 0.13 Wt % of Hydrogen Peroxide Water A 200 ml glass, three-necked flask equipped with a condenser and a flask for drawing out was charged with 180 g of the colored main distillate ($S_2O_3$=1.18 mmol), 0.24 g (2.12 mols, about 2.12 equivalents relative to $S_2O_3$) of 30% hydrogen peroxide water, 6.24 g of water, and 1.5 g of $SiO_2$, followed by conducting distillation. At a temperature of the inside of the reactor of 76° C., a degree of decompression of 0.8 kPa and a column top temperature of 50-51° C., the initial distillate was taken out by 14 g. After that, it was started to take the main distillate. At a temperature of the inside of the reactor of 77° C., a degree of decompression of 0.8 kPa and a column top temperature of 50-51° C., 88 g of the main distillate was obtained. The obtained main distillate was 99.9% in purity of trifluoromethanesulfonic acid and visually transparent. As a result of calculating the S2O3 concentration by the UV measurement, the $S_2O_3$ concentration was 1 ppm or lower. Thus, the decolorization was found possible by conducting a distillation with the addition of 30% hydrogen peroxide water. Furthermore, as a result of adding fuming sulfuric acid to this reaction liquid, a blue color coloration derived from the reaction of $S+SO_3 \rightarrow S_2O_3$ did not occur. Therefore, no sulfur mixing was confirmed, either.

Example 2

[Step 2] Addition Distillation: Addition of 1 Wt % of Hydrogen Peroxide Water

It was conducted under the same conditions except in that 3.00 g (26.46 mmol, about 13.43 equivalents relative to S2O3) of 30% hydrogen peroxide water was used relative to 300 g (S2O3 concentration: 735 ppm) of the colored main distillate containing trifluoromethanesulfonic acid and $S_2O_3$, which was obtained by Step 1 of Example 1. The obtained main distillate was 99.9% in purity of trifluoromethanesulfonic acid. The $S_2O_3$ concentration was 1 ppm or lower. No sulfur mixing was found, either.

Example 3

[Step 2] Addition Distillation: Addition of 3.6 Wt % of Hydrogen Peroxide Water

It was conducted under the same conditions except in that 5.80 g (51.15 mmol, about 48.71 equivalents relative to $S_2O_3$) of 30% hydrogen peroxide water was used relative to 160 g ($S_2O_3$ concentration: 735 ppm) of the colored main distillate containing trifluoromethanesulfonic acid and $S_2O_3$, which was obtained by Step 1 of Example 1. The obtained main distillate was 99.9% in purity of trifluoromethanesulfonic acid. The $S_2O_3$ concentration was 1 ppm or lower. No sulfur mixing was found, either.

Example 4

[Step 2] Addition Distillation: Addition of Ozone

In place of the addition of 30% hydrogen peroxide water, bubbling was conducted by an ozone generator relative to the colored main distillate containing trifluoromethanesulfonic acid and $S_2O_3$, which was obtained by Step 1 of Example 1. After feeding all of the materials, the inside temperature was heated until about 90° C., and the stirring was conducted for 560 minutes under ozone bubbling (the amount of ozone introduced: about 4.0 mmol). Then, the same distillation operation was conducted to obtain the main distillate. The obtained main distillate was 99.9% in purity of trifluoromethanesulfonic acid. The $S_2O_3$ concentration was 1 ppm or lower. No sulfur mixing was found, either.

Example 5

[Step 1] Acid Decomposition

A 1000 ml reaction container made of SUS304 and equipped with a condenser and a flask for drawing out was charged with 840 g of sulfuric acid. There 460 g of potassium trifluoromethanesulfonate (composition: a high-purity product containing 0.1% of water) was added. Simultaneously with the reaction, a distillation was started. At a temperature of the inside of the reactor of 130° C., a degree of decompression of 3.5 kPa and a column top temperature of 72° C., the initial distillate was taken out by 30 g. After that, it was started to take the main distillate. At a temperature of the inside of the reactor of 140-152° C., a degree of decompression of 3.2-3.5 kPa and a column top temperature of 68-70° C., 220 g of the main distillate containing 97.5% of trifluoromethanesulfonic acid was obtained. This main distillate did not have a color in visual observation, but it was colored blue by adding fuming sulfuric acid. The $S_2O_3$ concentration was 90 ppm.

[Step 2] Discoloration Distillation: Addition of 0.02 Wt % of Hydrogen Peroxide Water A 200 ml glass, three-necked flask equipped with a condenser and a flask for drawing out was charged with 180 g of the colored main distillate ($S_2O_3$=0.14 mmol) containing trifluoromethanesulfonic acid and $S_2O_3$, which was obtained by Step 1, and 0.04 g (0.35 mmol, about 2.50 equivalents relative to $S_2O_3$) of 30% hydrogen peroxide water, followed by conducting distillation. At a temperature of the inside of the reactor of 76° C., a degree of decompression of 1.0 kPa and a column top temperature of 49-51° C., the initial distillate was taken out by 12 g. After that, it was started to take the main distillate. At a temperature of the inside of the reactor of 77° C., a degree of decompression of 0.8 kPa and a column top temperature of 50-51° C., 94 g of the main distillate was obtained. The obtained main distillate was 99.9% in purity of trifluoromethanesulfonic acid. The $S_2O_3$ concentration was 1 ppm or lower. Therefore, no sulfur mixing was found, either.

Comparative Example 1

Water Addition Distillation

The acid decomposition and [Step 2] were conducted under the same conditions except in that the addition of 0.24 g of 30% hydrogen peroxide water of Example 1 was not conducted. As a result of adding fuming sulfuric acid to the obtained main distillate, it was colored blue. Furthermore, sulfur precipitated in accordance with the reaction of the following scheme was confirmed sticking to the condenser section of the distillation column. When conducting the distillation in series, it is expected to have contamination of the main distillate, clogging of pipeline, etc. Therefore, a stable operation is difficult.

$S_2O_3+H_2O \rightarrow S\downarrow+H_2SO_4$ $S+SO_3 \rightarrow S_2O_3$ (coloring with a blue color)

Reference Example 1

In the following, a method for obtaining a fluoroalkanesulfonate used in Examples is described (the method disclosed in Patent Publication 2).

Using an electrolytic fluorination tank, an electrolytic fluorination was conducted by continuously adding $CH_3SO_2F$ by 285 g/hr and anhydrous hydrofluoric acid by 276 g/hr and setting the tank temperature at 10° C., 5.0 V, 500 Amp, and the reflux condenser at −40° C. As a result, a mixed gas containing 74.6 wt % of $CF_3SO_2F$ with hydrogen was obtained. This gas was firstly washed by water in a scrubber having a liquid surface area of 0.01 m2 per 1 L of gas to completely remove HF.

Then, at G=0.15 mol/hr·m², it was introduced into an iron scrubber packed with Raschig rings (made of SUS). An absorption reaction was conducted by supplying an aqueous solution containing 21.5 wt % of KOH and 7.0 wt % of $CF_3SO_3K$ at 3.06 kg/hr, thereby drawing out at 3.47 g/hr an absorption hydrolysis liquid containing $CF_3SO_3K$ at a concentration of 20.9 wt %.

Furthermore, $CF_3SO_2F$ was not detected at all in the gas at the outlet of the scrubber.

Out of 2.8 kg of this absorption hydrolysis liquid, 0.82 kg of water was distilled by an evaporator, followed by cooling at 25° C. With this, crystals were precipitated. This slurry was subjected to a filtration separation by a centrifugal separator. With this, 0.47 kg of crystals containing 92.3 wt % of $CF_3SO_3K$ was obtained. The water content and KF and KOH contents of these crystals were 4.0 wt %, 1.7 wt % and 2.0 wt %, respectively. The obtained crystals can be used as the raw material of the acid decomposition.

The invention claimed is:

1. A method for producing a fluoroalkanesulfonic acid represented by the general formula [1], $$R^f SO_3H \quad [1]$$

wherein $R^f$ represents a $C_{1-4}$ straight chain or $C_{3-4}$ branched chain fluoroalkyl group, the method comprising:

(1) reacting concentrated sulfuric acid and/or fuming sulfuric acid with a fluoroalkanesulfonate represented by the general formula [2], $$(R^f SO_3)_n M \quad [2]$$

to cause an acid decomposition, thereby obtaining a reaction mixture containing the fluoroalkanesulfonic acid and a sulfur component, wherein $R^f$ is identical with that of the general formula [1], M represents an alkali metal or an alkali earth metal, and n is an integer of 1 or 2; and (2) adding an oxidizing agent selected from the group consisting of hydrogen peroxide and ozone to the reaction mixture obtained by step (1) and then conducting a distillation, thereby obtaining the fluoroalkanesulfonic acid from the reaction mixture.

2. A method for producing a fluoroalkanesulfonic acid represented by the formula [3], $$CF_3SO_3H \quad\quad [3]$$

the method comprising:

(1) reacting concentrated sulfuric acid and/or fuming sulfuric acid with a fluoroalkanesulfonate represented by the general formula [4], $$(CF_3SO_3)_nM \quad\quad [4]$$

to cause an acid decomposition, thereby obtaining a reaction mixture containing the fluoroalkanesulfonic acid and a sulfur component, wherein M represents an alkali metal or an alkali earth metal, and n is an integer of 1 or 2; and (2) adding an oxidizing agent selected from the group consisting of hydrogen peroxide and ozone to the reaction mixture obtained by step (1) and conducting a distillation, thereby obtaining the fluoroalkanesulfonic acid from the reaction mixture.

3. A method for producing a fluoroalkanesulfonic acid represented by the general formula [1], $$R^fSO_3H \quad\quad [1]$$

wherein $R^f$ represents a $C_{1-4}$ straight chain or $C_{3-4}$ branched chain fluoroalkyl group, the method comprising:

(1) reacting concentrated sulfuric acid and/or fuming sulfuric acid with a fluoroalkanesulfonate represented by the general formula [2], $$(R^fSO_3)_nM \quad\quad [2]$$

to cause an acid decomposition, thereby obtaining a reaction mixture containing the fluoroalkanesulfonic acid and a sulfur component, wherein $R^f$ is identical with that of the general formula [1], M represents an alkali metal or an alkali earth metal, and n is an integer of 1 or 2; and (2) adding an oxidizing agent to the reaction mixture obtained by step (1) and then conducting a distillation, thereby obtaining the fluoroalkanesulfonic acid from the reaction mixture, wherein the oxidizing agent in step (2) is hydrogen peroxide.

4. The method as claimed in claim 1, wherein in step (1), when concentrated sulfuric acid and/or fuming sulfuric acid is reacted with the fluoroalkanesulfonate represented by the general formula [2], a silica compound is added.

5. The method as claimed in claim 1, wherein in step (2), water is added together with the oxidizing agent to conduct the distillation.

6. The method as claimed in claim 1, wherein, in producing the fluoroalkanesulfonic acid, the fluoroalkanesulfonate represented by the general formula [2] is one obtained by reacting at least one selected from the group consisting of alkali metal hydroxides, alkali metal carbonates, alkali metal hydrogencarbonates, alkali earth metal hydroxides, alkali earth metal carbonates, and alkali earth metal hydrogencarbonates, with a fluoroalkanesulfonyl halide represented by the general formula [5], $$R^fSO_3X \quad\quad [5]$$

wherein Rf is identical with that of the general formula [1], and X represents fluorine, chlorine, bromine, or iodine.

7. The method as claimed in claim 1, wherein the sulfur component is sulfur or disulfur trioxide.

8. The method as claimed in claim 1, wherein in steps (1) or (2), the sulfur component is sulfur or disulfur trioxide, and the oxidizing agent is 1-100 equivalents relative to 1 mol of the disulfur trioxide.

9. The method as claimed in claim 5, wherein in step (2), the water is 0.1-30 mass %.

* * * * *